United States Patent
Yasui et al.

(10) Patent No.: US 9,772,264 B2
(45) Date of Patent: Sep. 26, 2017

(54) AUTOMATIC ANALYZER

(75) Inventors: Akihiro Yasui, Tokyo (JP); Kazuhiro Nakamura, Tokyo (JP); Hitoshi Tokieda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 441 days.

(21) Appl. No.: 14/241,148

(22) PCT Filed: May 17, 2012

(86) PCT No.: PCT/JP2012/062670
§ 371 (c)(1),
(2), (4) Date: Mar. 20, 2014

(87) PCT Pub. No.: WO2013/042404
PCT Pub. Date: Mar. 28, 2013

(65) Prior Publication Data
US 2014/0199779 A1    Jul. 17, 2014

(30) Foreign Application Priority Data
Sep. 22, 2011   (JP) ................................. 2011-207745

(51) Int. Cl.
*G01N 1/28* (2006.01)
*G01N 35/10* (2006.01)

(52) U.S. Cl.
CPC ........... *G01N 1/28* (2013.01); *G01N 35/1011* (2013.01); *G01N 2035/1025* (2013.01); *Y10T 436/2575* (2015.01)

(58) Field of Classification Search
None
See application file for complete search history.

(56) References Cited

U.S. PATENT DOCUMENTS 5,133,392 A * 7/1992 Hamann ............... B01L 3/0262
                                                        141/1
6,270,726 B1 * 8/2001 Tyberg ............... G01N 35/1011
                                                        422/509

(Continued)

FOREIGN PATENT DOCUMENTS

JP      11-160326 A    6/1999
JP      11-160327 A    6/1999

(Continued)

OTHER PUBLICATIONS

Extended European Search Report received in corresponding European Application No. 12834325.8 dated Mar. 25, 2015.
International Preliminary Report on Patentability received in International Application No. PCT/JP2012/062670 dated Apr. 3, 2014.

*Primary Examiner* — Sean E Conley
*Assistant Examiner* — Benjamin R Whatley
(74) *Attorney, Agent, or Firm* — Mattingly & Malur, PC (57) ABSTRACT

An automatic analyzer is capable of controlling the gap between the tip of the sample nozzle and the bottom surface of the reaction container and restricting the sample attached to the tip of the sample nozzle. A movement distance of an arm is calculated and stored while the tip of the sample nozzle contacts a coordinate measurement stand until a stop position detector detects a stop position detection plate. The sample nozzle is moved toward the bottom surface of the reaction container and is stopped at the time when the stop position detector detects the stop position detection plate. The arm is moved upwardly for the movement distance stored in memory from this position. The sample nozzle can be stopped such that the tip of the sample nozzle is contacted to the bottom surface of the reaction container and the bend (warp) of the sample nozzle is restricted.

7 Claims, 7 Drawing Sheets

(56) References Cited

U.S. PATENT DOCUMENTS

| | | | |
|---|---|---|---|
| 6,363,802 B1* | 4/2002 | Grippo | G01N 35/1011 73/864.24 |
| 2001/0028864 A1* | 10/2001 | Tyberg | G01N 35/1011 422/509 |
| 2003/0187600 A1* | 10/2003 | Barnes | G01N 35/10 702/85 |
| 2007/0012123 A1* | 1/2007 | Li | G01N 35/1016 73/863.01 |
| 2009/0068062 A1 | 3/2009 | Jafari et al. | |
| 2011/0223061 A1* | 9/2011 | Oonuma | G01N 35/10 422/62 |
| 2012/0114526 A1* | 5/2012 | Watanabe | G01F 23/00 422/63 |
| 2012/0156098 A1* | 6/2012 | Sano | G01N 35/10 422/68.1 |
| 2012/0321520 A1* | 12/2012 | Okanojo | G01N 21/6428 422/82.08 |

FOREIGN PATENT DOCUMENTS

| | | | | |
|---|---|---|---|---|
| JP | 11-304819 A | 11/1999 | | |
| JP | 2003-322656 A | 11/2003 | | |
| JP | 2003-344426 A | 12/2003 | | |
| JP | 2003-344427 A | 12/2003 | | |
| JP | 2003344426 A | * 12/2003 | | |
| JP | 2010-175417 A | 8/2010 | | |
| JP | WO 2010095375 A1 | * 8/2010 | | G01F 23/00 |
| JP | 2010-236967 A | 10/2010 | | |
| JP | 2010-271203 A | 12/2010 | | |
| JP | 2010271203 A | * 12/2010 | | |
| JP | WO 2011030616 A1 | * 3/2011 | | G01N 35/10 |
| JP | WO 2011104986 A1 | * 9/2011 | | G01N 35/1011 |
| WO | 2013/006343 A1 | 1/2013 | | |

* cited by examiner

FIG. 1

1. REACTION DISK
2. REACTION CONTAINER
3. WASHING MECHANISM
4. SPECTROPHOTOMETER
5. MIXING MECHANISM
6. MIXING MECHANISM
7. REAGENT DISPENSING MECHANISM
8. REAGENT DISPENSING MECHANISM
9. REAGENT DISK
10. REAGENT BOTTLE
11. SAMPLE DISPENSING MECHANISM
11a. SAMPLE NOZZLE
13. WASHING TANK
15. SAMPLE CONTAINER
16. RACK
17. SAMPLE TRANSFERRING MECHANISM
18. REAGENT PUMP
19. SAMPLE PUMP
20. WASHING PUMP
21. CONTROLLER
30. WASHING TANK
31. WASHING TANK
32. WASHING TANK
33. WASHING TANK
47. COORDINATE MEASURING POSITION

FIG. 2

11a. SAMPLE NOZZLE
41. UP DOWN ROTATION MECHANISM
42. ARM
43. STOP POSITION DETECTION PLATE
44. STOP POSITION DETECTOR
45. ELASTIC BODY
46. CAPACITANCE DETECTOR

AUTOMATIC ANALYZER

TECHNICAL FIELD

The present invention relates to an automatic analyzer quantitatively or qualitatively analyzing components of blood, urine or the like.

BACKGROUND ART

An automatic analyzer quantitatively or qualitatively analyzing specific components included in blood, urine or the like is necessary for a present diagnosis in view of the repeatability of an analysis result, high process speed or the like.

The measuring methods of an automatic analyzer are classified roughly into an analysis method (the colorimetric analysis) using a reagent reacting the analysis object component of a sample to change the color of the reaction solution, and an analysis method (the immunity analysis) using a reagent adding markers into materials specifically binding object components directly or indirectly to count the markers.

In every analysis methods, the predetermined amount of regent is mixed into a sample to execute an analysis. Recently, an analysis apparatus is required to reduce the amount of reagents used for an analysis in response to the request for reducing the cost of the analysis. The amount of a sample used for one analysis in the present automatic analyzer is a digit micro litter order, and the maintenance of the high dispensing accuracy is required at the same time.

According to the method described in the Patent Document 1 for maintaining the high reliability in the low dispensing amount about 1 micro litter, after a sample is discharged in a sample container, a nozzle is moved at a low speed until the nozzle is separated from the sample, so that the amount of the sample attached to the nozzle is reduced to improve the dispensing accuracy of the sample.

Further, according to a method described in the Patent Document 2, when a sample is discharged into a reaction container, the gap between the bottom of the reaction container and the tip of a sample probe is kept at a constant value, and the sample probe is moved upwardly while the sample probe dispenses the sample, so that the sample is prevented from attaching to the side surface of the sample probe to improve the dispensing accuracy.

PRIOR ART DOCUMENTS

Patent Document

Patent Document 1: JP2010-271203A
Patent Document 2: JP2010-175417A

SUMMARY OF THE INVENTION

Problems to be Solved by the Invention

However, the above-mentioned prior art includes problems described below.

According to the technique described in the Patent Document 1, the moving distance of a nozzle at low speed is the distance to the nozzle separating position from the discharged sample in order to prevent the throughput of the apparatus at per time from lowering. The patent Document 1 does not fully describe the upwardly moving distance of the nozzle required to be separated from the sample.

Further, the Patent Document 1 describes that the nozzle is moved downwardly to the vicinity of the bottom surface of the reaction container. In an actual apparatus, several hundred reaction containers are set along a circle, it is difficult to keep the heights of all bottom surfaces of the reaction containers at a constant values. Therefore, it is a general way that the nozzle is supported by an elastic body, and the nozzle is moved downwardly to elastically contact to all reaction containers. The sample nozzle is required to move at a low speed on a way including the distance required for elastically contacting operation. Therefore, it is a long time to separate the nozzle from the sample.

Further, there are individual difference of the length of a nozzle, and the relative position between the tip of the nozzle and the reaction container is changed by the mounting operation, the demounting operation, and the exchanging operation of the nozzle, so that the position correcting operation with respect to the reference position or the elastic contact distance lengthening operation is required, and the latter operation makes the moving distance at low speed to be further long.

For example, if the moving speed of the nozzle at low speed is 10 mm/s, 0.1 second is added to the moving time in case that 1 mm is added to the moving distance. It causes that the throughput per unit time is lowered.

Further, when the nozzle is moved upwardly and the condition of the nozzle is returned to the original condition (no bended condition of the nozzle) from the elastic contact condition (bended (warped) condition of the nozzle), the nozzle is vibrated. It is possible that the sample attached to the side surface of the nozzle is scattered to the side surface of the reaction container.

Further, in the technique described in the Patent Document 2, when a sample is discharged into a reaction container, the gap between the bottom surface of the reaction container and the tip of the sample probe is kept to a constant value, and the sample probe is moved upwardly during the sample dispensing operation, so that the sample is prevented from attaching to the side surface of the sample probe, and the dispensing accuracy is improved. According to the above-mentioned method, the operations of the sample probe and a pump used for a sample must be synchronized with each other. It is difficult to control.

Further, how to moisture and to spread the sample discharged from the sample probe at the bottom surface of the reaction container is changed by the change of the wettability caused by a dirt, scratch or the like of the bottom surface of the reaction container to the sample and the effect of the residual water after the reaction container washing operation, so that it is very difficult to control the distance between the tip of the nozzle and the bottom surface of the reaction container and the distance between the surface of the liquid of the discharged sample and the bottom surface of the reaction container to be equal with each other.

Further, since sample probe is moved upwardly during the sample discharging operation, the vibration of the sample probe at the upward moving operation possibly effect the dispensing accuracy.

The object of the present invention is to realize an automatic analyzer and a sample dispensing method in an automatic analyzer capable for controlling the gap between the tip of the sample nozzle and the bottom surface of the reaction container for each sample dispensing operation without relationship of the individual difference of a reaction container or a sample nozzle, and capable for restricting the sample attached to the tip of the sample nozzle.

Means for Solving the Problems

The construction of the present invention attaining the above object is as follows:

A sample nozzle is moved downwardly to a reaction container, and the sample nozzle is elastically contacted to the reaction container, and the sample nozzle is stopped by a stop position detector. After the sample nozzle is stopped, the sample nozzle is moved upwardly to the elastic contact start point of the reaction container. With respect to the start of the sample discharging operation, the sample discharging operation may be started after the nozzle was moved upwardly and reached to the elastic contact start point, and the sample discharging operation may be started before the nozzle is moved upwardly. In the latter case, when the discharging time of the latter case is equal to the discharging time of the former case, the time required to complicate the discharging operation after the sample nozzle is stopped by an obstacle detector can be shortened in comparison with former case.

With respect to the upward distance to the elastic contact start point, the stop position detected by a capacitance detector and the stop position detected by the stop position detector are stored at a coordinate measuring position, the difference between the above stop positions.

After the sample discharge operation, the sample nozzle is moved at a low speed until the tip of the sample nozzle is separated from the sample, the sample nozzle is moved at high speed after the tip of the nozzle is separated from the sample.

Effects of the Invention

According to the present invention, since the sample nozzle is positioned at the elastic contact start position of the bottom of the reaction container (the sample nozzle and the bottom of the container are in the contact condition) at the operation of the sample discharging into the reaction container without relationship of the individual difference of the sample nozzle, the sample nozzle is not vibrated, and the sample can be discharged to spread the sample on the bottom of the reaction container to wet the bottom of the reaction container certainly. Further, after the sample is discharged, the sample nozzle can be separated from the sample along the minimum low speed moving distance, and the moving time at low speed can be saved.

MODE FOR CARRYING OUT THE INVENTION

The mode for carrying out the present invention will be described herein under with reference to the drawings.

Embodiments

Figure 1:
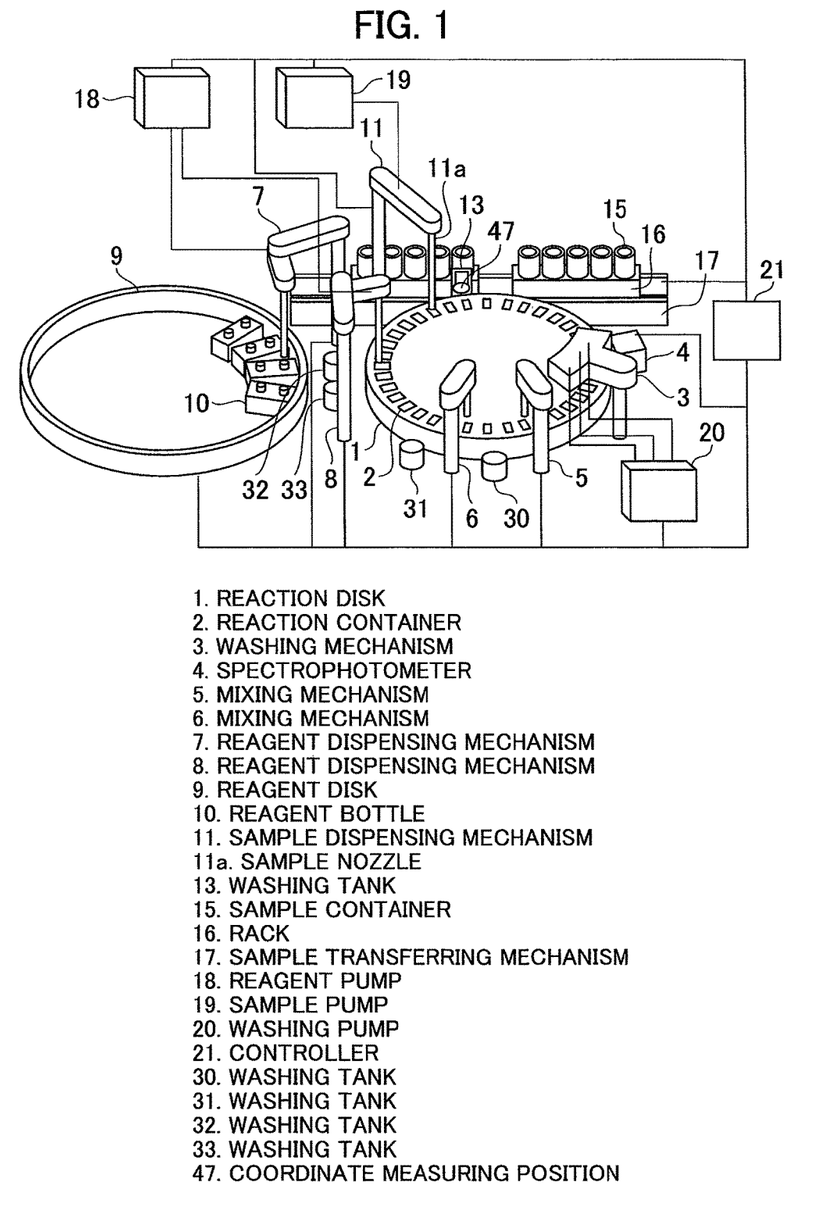
FIG. 1 is a schematic construction drawing of an automatic analyzer to which the present invention is applied.

FIG. 1 is a schematic construction drawing of an automatic analyzer to which the present invention is applied.

In FIG. 1, reaction containers 2 are arranged along a circular on a reaction disk 1. Plural reagent bottles 10 can be arranged along a circular in a reagent disk 9. A sample transferring mechanism 17 is set on the vicinity of the reaction disk 1, transferring a rack 16 mounting sample containers 15. Reagent dispensing mechanisms 7 and 8 are set between the reaction disk 1 and the reagent disk 9.

Further, a sample dispensing mechanism 11 capable for rotating and moving up and down is set between the reaction disk 1 and the sample transferring mechanism 17, the sample dispensing mechanism 11 including a sample dispensing nozzle (a sample nozzle for short) 11a. A sample pump 19 is connected to the sample nozzle 11a. The sample nozzle 11a rotates and moves to trace a circular arc having a rotational axis to dispense the reagent into the reaction container 2 from the sample container 15.

A washing mechanism 3, a spectrophotometer 4, mixing mechanisms 5 and 6, the reagent disk 9, and the sample transferring mechanism 17 are arranged on the periphery of the reaction disk 1, a washing pump 20 being connected to the washing mechanism 3. Washing tanks 13, 30, 31, 32, and 33 are set on the range of the motions of the reagent dispensing mechanisms 7 and 8, the sample dispensing mechanism 11, the mixing mechanisms 5 and 6 respectively. A reagent pump 18 is connected to the reagent dispensing mechanisms 7 and 8.

Inspection samples of blood or the like are received in the sample container 2, the sample container 2 being mounted on the rack 16 to be transferred by the sample transferring mechanism 17. Further, each mechanism is connected to a controller 21, the operation of each mechanism being controlled by the controller 21. Further, the controller 21 includes functions as an analysis section for analyzing an inspection sample in the reaction container 2.

A coordinate measuring stand 47 is arranged at the vicinity of the washing tank 13.

Figure 2:
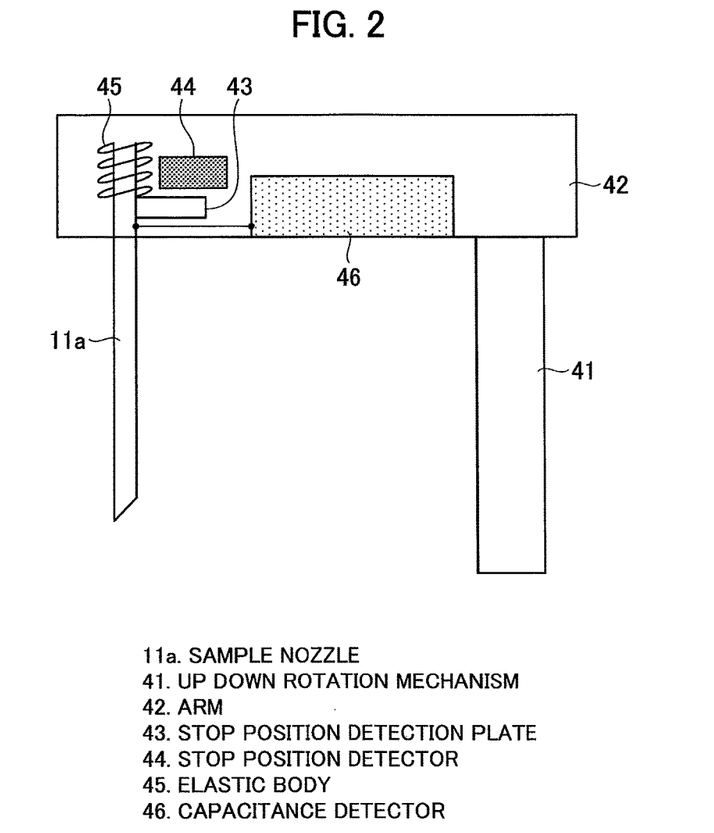
FIG. 2 is a schematic construction drawing of a sample dispensing mechanism 11 in one embodiment of the present invention.

FIG. 2 is the schematic construction drawing of the sample dispensing mechanism 11 in one embodiment of the present invention. In FIG. 2, the sample dispensing mechanism 11 includes the sample nozzle 11*a* for sucking and discharging the sample, an arm 42 holding the sample nozzle 11*a*, an elastic body 45 elastically supporting the sample nozzle 11*a*, a capacitance detector 46 detecting the capacitance change of the sample nozzle Ha, a stop position detection plate 43 connected to the sample nozzle 11*a*, a stop position detector 44 set on the arm 42 to detect the movement of the stop position detection plate 43, and an up down rotation mechanism 41 executing the up, down, and rotation operation of the arm 42. The stop position detection plate 43 and the stop position detector 44 may be used for as an obstacle detection plate and an obstacle detector, and the stop position detection plate 43 and the stop position detector 44 can be set in independent of an obstacle detection plate and an obstacle detector.

Figure 3:
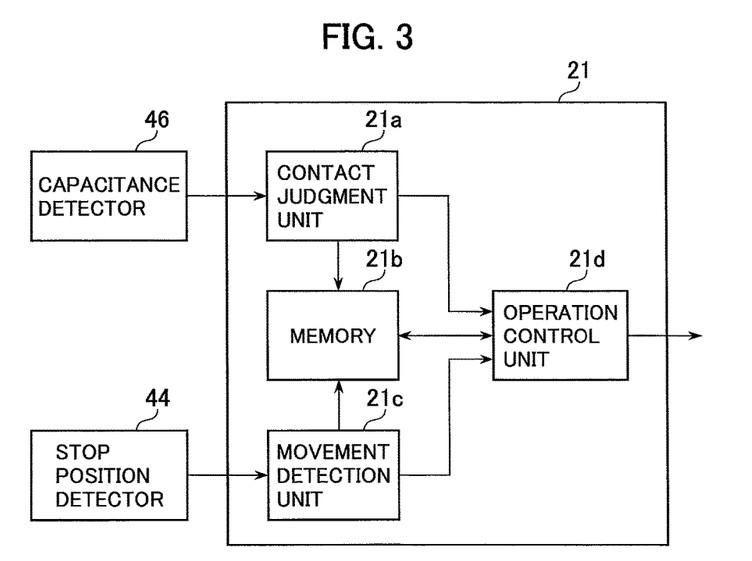
FIG. 3 is a drawing of the inner construction of a controller 21 in one embodiment of the present invention.

FIG. 3 is a drawing of the inner construction of a controller 21 in one embodiment of the present invention. In FIG. 3, the capacitance detection signal from the capacitance detector 46 is supplied to the controller 21, the controller 21 including a contact judgment unit 21*a* judging the contact between the sample nozzle 11*a* and the liquid surface or a material body when the capacitance detection signal changes more than or equal to a constant value, a movement detection unit 21*c* to which the stop position detection signal is supplied from the stop position detector 44, a memory 21*b*, and an operation control unit 21*d* controlling the operation of the sample nozzle 11 on the basis of the signals from the contact judgment unit 21*a* and the stop position detector 44 and the data stored in the memory 21*b*. The controller 21 includes the function for controlling the operations of the reaction disk 1 or other mechanisms.

Figure 13:
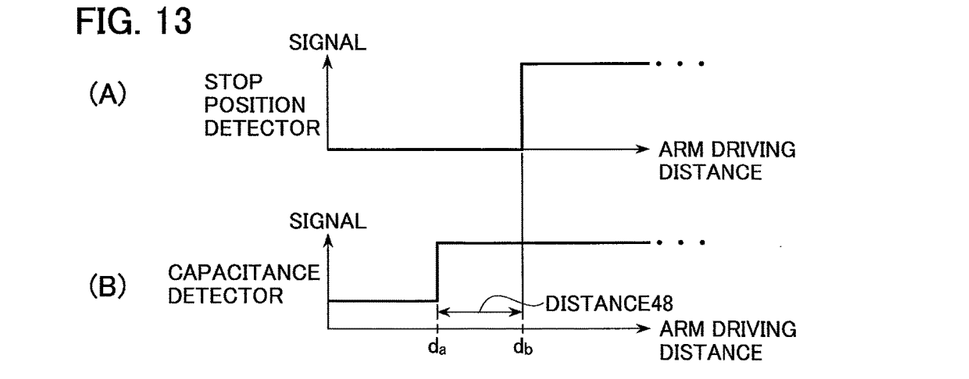
FIG. 13 is a drawing for explaining the relationship between the output signals of a stop position detector and a capacitance detector, and the arm driving distance.

Next, the method for measuring the elastic movement distance 48 in one embodiment of the present invention will be described with reference to FIGS. 4, 5, and 13.

Figure 4:
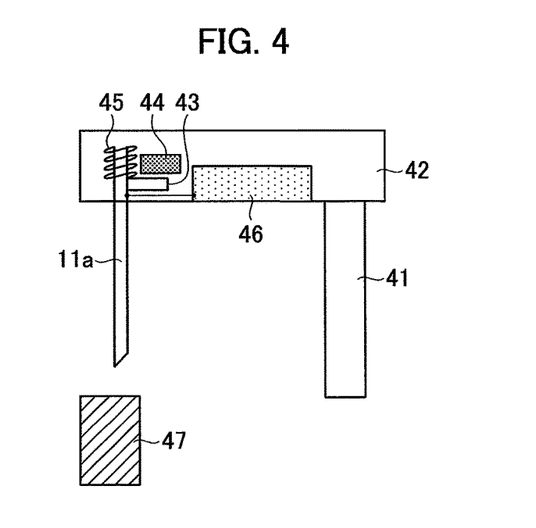
FIG. 4 is a drawing for explaining the measuring method of an elastic contact movement distance 48 in one embodiment of the present invention.

As shown in FIG. 4, the arm 42 and the sample nozzle 11*a* are downwardly moved toward the coordinate measuring stand 47 by the up down rotation mechanism 41. When the tip of the sample nozzle 11*a* contacts to the coordinate measuring stand 47, the capacitance detector 46 detects the change of the capacitance (an arm driving distance da), as shown in (B) of FIG. 13. When the contact judgment unit 21*a* judges the change of the capacitance, the operation control unit 21*d* stops the downward movement of the arm 42 and the sample nozzle 11*a*. The operation stop position is stored in the memory 21*b*.

The coordinate measuring stand 47 is made of an electrical conductive material, for example a metal, or an electrical conductive plastic desirably in order to measure the capacitance change. The coordinate measuring stand 47 is made of an electrical conductive material. It is the reason that the electrical conductive material can easily detect the capacitance change when the nozzle 11*a* contacts to the coordinate measuring stand 47. As described herein after, it is difficult to judge the contact between the nozzle and the bottom portion of the reaction container 2 by using the capacitance detector 46, so that the conductivity of the material of the coordinate measuring stand 47 is desirably higher than the material used as the reaction container 2 at least. Further, the coordinate measuring stand 47 is connected to the ground desirably in order to easily detect the change of the capacitance.

Figure 5:
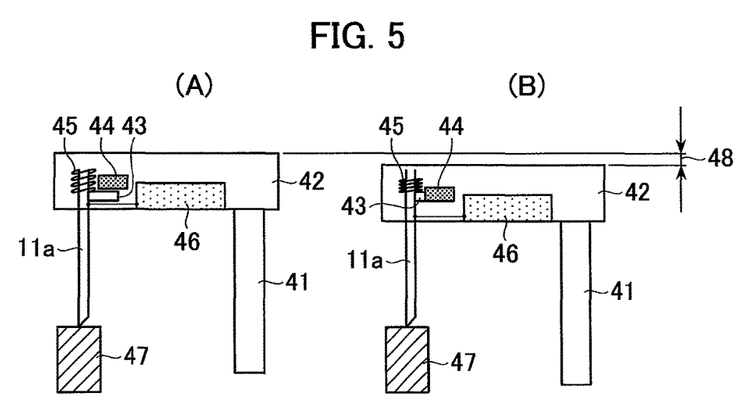
FIG. 5 is a drawing for explaining the measuring method of the elastic contact movement distance 48 in one embodiment of the present invention.

Next, as shown in (A) of FIG. 5, the arm 42 is further moved downwardly by the up down rotation mechanism 41 from the condition that the tip of the sample nozzle 11*a* is contacted to the coordinate measuring stand 47, and the arm 41 is moved downwardly while the sample nozzle 11*a* is elastically contacted to the coordinate measuring stand 47, that is, the elastic force of the elastic body 45 is applied to the arm 41. Further, as shown in (B) of FIG. 5, when the stop position detection plate 43 enters into the detection area of the stop position detector 44, the signal of the stop position detector 44 changes (the arm driving distance db) as shown in (A) of FIG. 13, and the movement detection unit 21*c* judges the change of the signal, and the operation control unit 21*d* stops the downward movement of the arm 42.

The position of the sample nozzle 11*a* at this time is stored in the memory 21*b*. It can be assumed a sensor such as a photo interrupter is used as the stop position detector 44.

The operation control unit 21*d* calculates the elastic contact movement distance 48 of the sample nozzle 11*a* from the stop position information stored in the memory 21*b* of the controller 21, and the elastic contact movement distance 48 of the sample nozzle 11*a* is the distance from the contact position of the sample nozzle 11*a* with the coordinate measuring stand 47 to the stop position detection plate 43 detected position detected by the stop position detector 44. This distance is the difference between the stop position detected by the capacitance detector 46 and the stop position detected by the stop position detector 44, as shown in FIG. 13. The calculated distance is stored in the memory 21*b*.

According to the above-described measuring method, the method can obtain the elastic contact movement distance 48 including the dispersion of the dimension of the sample nozzle 11*a* and the dispersion of the distance between the distance detected by the stop position detector 44 and the distance detected by the stop position detection plate 43. The above calculation is executed for each of automatic analyzers. Further, the above calculation is executed after the exchange operation of a nozzle or the like was executed.

Figure 6:
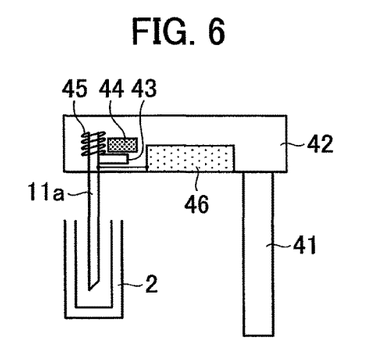
FIG. 6 is a drawing for explaining the method for moving a sample nozzle 11a for a reaction container 2 in one embodiment of the present invention.
Figure 7:
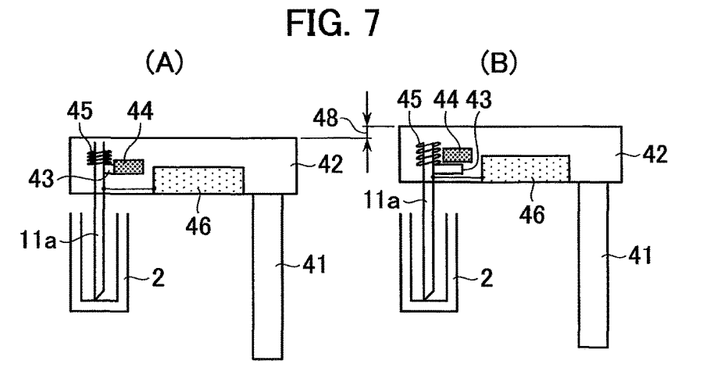
FIG. 7 is a drawing for explaining the method for moving the sample nozzle 11a for the reaction container 2 in one embodiment of the present invention.

FIGS. 6 and 7 are drawings for explaining the method for moving a sample nozzle 11*a* for a reaction container 2 in one embodiment of the present invention.

The sample nozzle 11*a*, which sampled the sample from the sample container 15, is downwardly moved toward the bottom portion of the reaction container 2, as shown in FIG. 6 after the sample nozzle 11*a* is moved toward the upper position of the reaction container 2 by the up down rotation mechanism 41. A glass or plastic having high permeability is mainly used as the material of the reaction container 2 in order to measure the solution in the reaction container 2 by using the spectrophotometer 4, so that it is difficult to detect the contact between the sample nozzle 11*a* and the bottom portion of the reaction container 2 by using the capacitance detector 46.

Therefore, the elastic contact operation of the sample nozzle 11*a* is executed after the sample nozzle 11*a* was contacted to the bottom portion of the reaction container 2, thereafter, the arm 42 is moved downwardly, and the arm 42 is stopped when the stop position 44 detects the stop position detection plate 43, as shown in (A) of FIG. 7.

Next, as shown in (B) of FIG. 7, the arm 42 is moved upwardly for the above-described elastic contact moving distance 48, so that the sample nozzle 11*a* can be moved to the elastic contact start point which is the contact point of the sample nozzle 11 *a* and bottom portion of the sample container 2.

The above-described method is used in the present invention, so that the automatic analyzer can control the operations that the position of the tip of the sample nozzle 11*a* is positioned at the elastic contact start point of the bottom surface of the sample container 2 without relationship of the individual difference of the dimensions of all reaction containers 2 set on the automatic analyzer.

Further, the sample nozzle 11*a* is moved to the elastic contact start point, so that the sample nozzle 11*a* is not vibrated because the bottom surface of the reaction container 2 and the sample nozzle 11*a* are contacted with each other even when the bended condition of the sample nozzle 11*a* is released.

Figure 8:
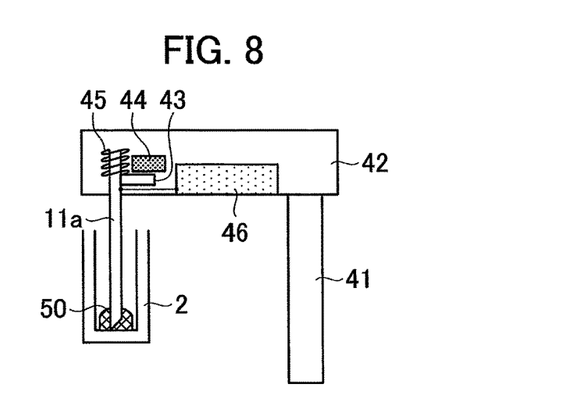
FIG. 8 is a drawing for explaining the method for discharging the sample into the reaction container 2 in one embodiment of the present invention.
Figure 9:
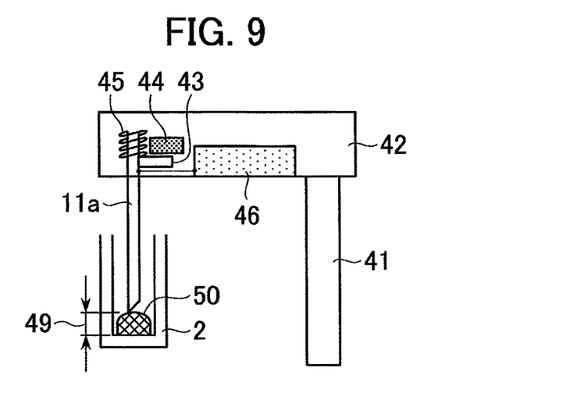
FIG. 9 is a drawing for explaining the method for discharging the sample into the reaction container 2 in one embodiment of the present invention.
Figure 10:
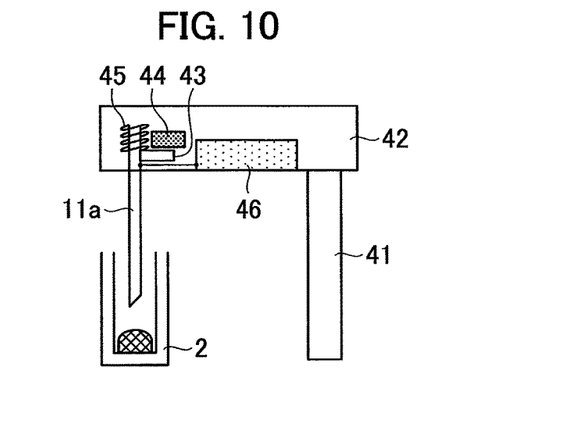
FIG. 10 is a drawing for explaining the method for discharging the sample into the reaction container 2 in one embodiment of the present invention.

FIGS. 8, 9, and 10 are drawings for explaining the method for discharging the sample into the reaction container 2 in one embodiment of the present invention.

As shown in FIG. 8, the sample is discharged from the sample nozzle 11*a* by the operation of the sample pump 19 on the basis of the commands from the controller 21 while the sample nozzle 11*a* is being stopped at the elastic contact start point of the bottom surface of the reaction container 2.

Figure 14:
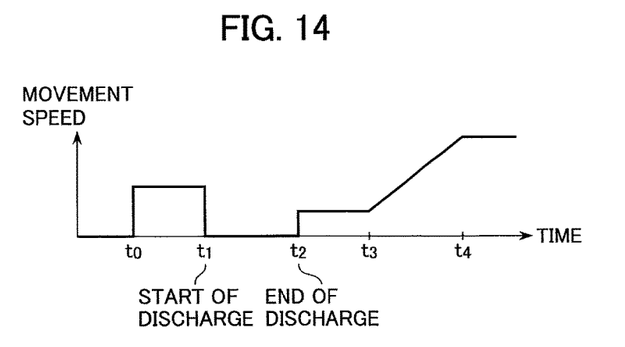
FIG. 14 is a drawing for explaining the relationship between the moving speed of the arm and time.

After the sample is discharged from the sample nozzle 11*a*, as shown in FIG. 9, the sample nozzle 11*a* is upwardly moved (between the time $t_3$ from time $t_2$ in FIG. 14) at low speed (for example, 10 mm/s) for the sample separating distance 49 required to separate the nozzle 11*a* from the discharged sample 50 on the bottom surface of the reaction container 2, as shown in FIG. 14. The times between the time $t_0$ to $t_1$ shown in FIG. 14 represent the movement from the condition shown in (A) of FIG. 7 to the condition shown in (B) of FIG. 7, and the times between the time $t_1$ to $t_2$ shown in FIG. 14 represent the condition shown in FIG. 8.

The sample separating distance 49 may be decided by the detection signal from the capacitance detector 46 or the like, and the sample separating distance 49 may be a distance corresponding to the height of the sample which can be calculated from the discharge volume of the sample. The separating distance is affected by not only the change of the wettability, which is caused by dirt or scratch, of the bottom surface of the reaction container 2 against the sample, and the residual water in the reaction container 2 after washing operation, but also the wettability of the sample nozzle 11*a* against the sample in case that the height of the sample calculated from the discharge volume is used as the sample separating distance 49, so that the extra movement distance is added to the sample separating distance 49 in view of the sample height calculated from the discharge volume desirably.

The sample nozzle 11*a* is moved for the sample separating distance (low speed moving distance), thereafter, the sample nozzle 11*a* is moved upwardly at a high speed (for example, 12 mm/s) by the up down rotation mechanism 41 to separate from the reaction container perfectly, as shown in FIGS. 10 and 14. After the sample nozzle 11*a* is moved for the low speed moving distance 49, the moving speed of the sample nozzle 11*a* is accelerated to 12 mm/s from 10 mm/s between the time t3 and time t4 shown in FIG. 14, thereafter, the sample nozzle 11*a* can be moved upwardly at the constant speed of 12 mm/s.

The sample discharging operation from the sample nozzle 11*a* into the reaction container 2 can be executed after the arm 42 is moved upwardly for the contact moving distance from the condition that the sample nozzle 11*a* contacts to the bottom surface of the reaction container 2 and the stop position detector 44 detects the stop position detection plate 43, as shown in (A) of FIG. 7. Further, the arm 42 can be moved upwardly while the sample is being discharged from the condition as shown in (A) of FIG. 7. Further, the sample is discharged from the condition as shown in (A) of FIG. 7 previously, thereafter, the arm 42 can be moved upwardly for the contact moving distance.

As described above, the sample nozzle 11*a* is operated as shown in FIGS. 4 to 10, 13, and 14, so that the sample nozzle 11*a* is positioned at the elastic contact start point on the bottom surface of the reaction container 2 without the relationship of the individual difference of the reaction container 2 and the sample nozzle 11*a* when the sample is discharged into the reaction container 2. Therefore, the sample nozzle 11*a* is not vibrated at the time of the sample discharge operation, and the sample can be discharged to moisture and to spread on the bottom surface of the reaction container 2.

Further, since the sample nozzle 11*a* can be separated from the sample form t the minimum low speed movement distance 49 after the sample is discharged into the reaction container 2, the improvement of the cycle time can be expected.

Figure 11:
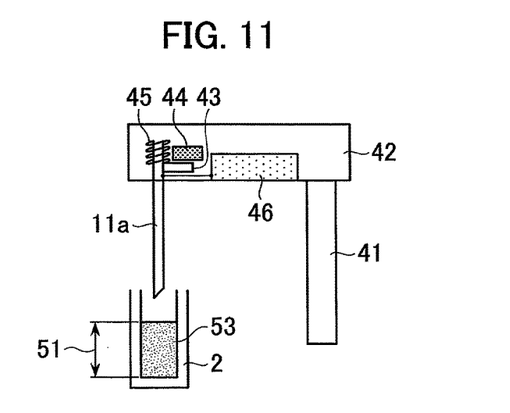
FIG. 11 is a drawing for explaining the other method for obtaining the elastic contact movement distance 48 in one embodiment of the present invention.
Figure 12:
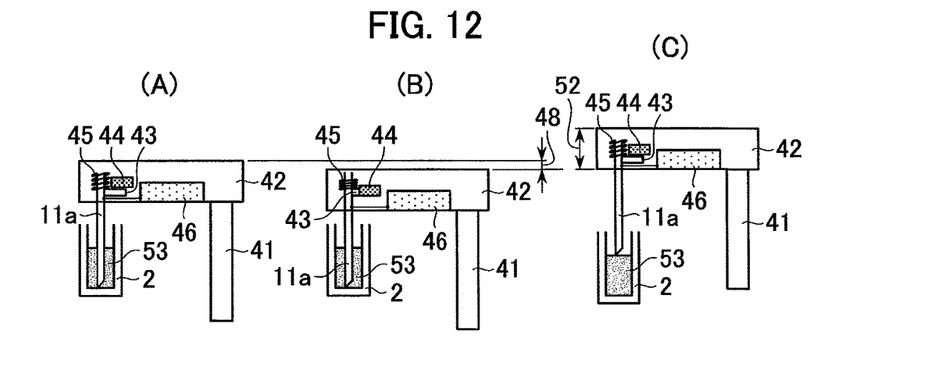
FIG. 12 is a drawing for explaining the other method for obtaining the elastic contact movement distance 48 in one embodiment of the present invention.
Figure 15:
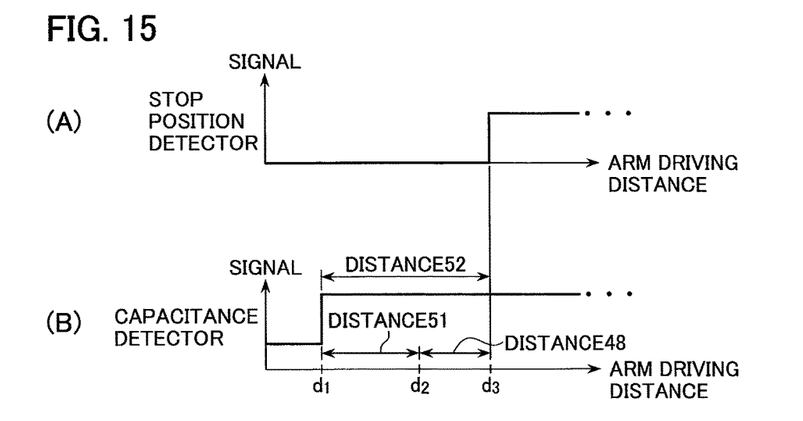
FIG. 15 is a drawing for explaining the relationship between the output signals of the stop position detector and the capacitance detector, and the arm driving distance.

FIGS. 11, 12, and 15 are drawings for explaining the other method for obtaining the elastic contact movement distance 48 in one embodiment of the present invention. This method is to obtain the elastic contact movement distance 48 without the usage of the coordinate measuring stand 47.

As shown in FIG. 11, the sample nozzle 11*a* is moved downwardly toward the reaction container 2 by the up down rotation mechanism 41. The solution 53, which was discharged by the dispensing mechanism of one of the sample dispensing mechanism 11, sample dispensing mechanism 7 or 8, exists in the reaction container 2.

The liquid height 51 of the solution 53 from the bottom surface of the reaction container 2 can be easily calculated from the discharge amount on any one of the dispensing mechanisms 11, 7, and 8 and the cross section of the reaction container 2.

The sample nozzle 11*a*, which was moved downwardly by the up down rotation mechanism 41, contacts the liquid surface of the solution 53, as shown in (C) of FIG. 12, and the contact between the sample nozzle and the liquid surface is detected by the capacitance detector 46, as shown in (B) of FIG. 15, and the sample nozzle 11*a* is stopped by the command of the controller 21, and the stop position at the liquid surface (the arm driving distance $d_1$) is stored in the memory 21*b* of the controller 21.

Next, the sample nozzle 11*a* is inserted into the solution 53 in the reaction container 2 to move downwardly by the up down rotation mechanism 41, and the sample nozzle 11*a* elastically contacts to the bottom surface of the reaction container 2 ((A) of FIG. 12), and the arm is further moved downwardly, and the sample nozzle 11*a* is stopped, as shown in (A) of FIG. 15, when the stop position detector 44 detects the stop position detection plate 43 ((B) of FIG. 12). The stop position at this time (the arm driving distance $d_3$ shown in (B) of FIG. 15) is stored in the memory 21*b* of the controller 21.

The elastic contact movement distance 48 of the sample nozzle 11*a* is the value calculated by subtracting the liquid height 51 ($d_2$) from the absolute value 52 (the ramming distance) which is the difference between the stop position ($d_1$) detected by the capacitance detector 46 an the stop position ($d_3$) detected by the stop position detector 44 on the basis of the stop position information and the liquid height 51 stored in the memory 21*b* of the controller 21, as described in (B) of FIG. 15. Namely, (the arm driving distance 52)–(the liquid height 51)=(the elastic contact distance 48).

The elastic contact distance 48 can be measured by using the above-mentioned method without the preparation of a special thing such as the coordinate measurement stand 47.

As described above, according to one embodiment of the present invention, the movement distance 48 of the arm 42 supporting the sample nozzle 11a is calculated and stored in the memory 21b, and the movement distance 48 is the distance when the tip of the sample nozzle 11a of the sample dispensing mechanism 11 contacts to the coordinate measurement sand 47 until the stop position detector 44 detects the stop position detection plate 43. If the coordinate measurement stand 47 is not used, the arm driving distance 52 of the arm 42 supporting the sample nozzle 11a is calculated, and the arm driving distance 52 is the distance when the tip of the sample nozzle 11a of the sample dispensing mechanism 11 contacts to the surface of the liquid in the reaction container 2 until the stop position detector 44 detects the stop position detection plate 43, and the height of the surface of the liquid in the reaction container 2 is subtracted from the calculated arm driving distance 52 to calculate the movement distance 48, and the calculated movement distance 48 is stored in the memory 21b.

Further, the sample nozzle 11a is moved for the bottom surface of the reaction container 2, and the movement of the sample nozzle 11a is stopped when the position detector 44 detects the stop position detection plate 43, and the arm 42 is moved upwardly for the movement distance 48 stored in the memory 21b from the stop position of the sample nozzle 11a. Accordingly, the sample nozzle 11a can be stopped at the condition that the tip of the sample nozzle 11a is contacted to the bottom surface of the reaction container 2 and the bending (warping) of the sample nozzle 11a is depressed.

Therefore, the present invention can realize an automatic analyzer and a sample dispensing method in an automatic analyzer capable for controlling the gap between the tip of the sample nozzle and the bottom surface of the reaction container for each sample dispensing operation without relationship the individual difference of a reaction container or a sample nozzle, and capable for restricting the sample attached to the tip of the sample nozzle.

DESCRIPTION OF REFERENCE NUMERALS

1 - - - Reaction disk, 2 - - - Reaction container, 3 - - - Washing mechanism, 4 - - - Spectrophotometer, 5,6 - - - Mixing mechanism, 7,8 - - - Reagent dispensing mechanism, 9 - - - Reagent disk, 10 - - - Reagent bottle, 11 - - - Sample dispensing mechanism, 13 - - - Washing mechanism, 15 - - - Sample container, 16 - - - Rack, 17 - - - Sample transferring mechanism, 18 - - - Reagent pump, 19 - - - Sample pump, 20 - - - Washing pump, 21 - - - Controller, 21a - - - Contact judgment unit, 21b - - - Memory, 21c - - - Movement detection unit, 21d - - - Operation control unit, 30 to 33 - - - Washing tank, 41 - - - Up down rotation mechanism, 42 - - - Arm, 43 - - - Stop position detection plate, 44 - - - Stop position detector, 45 - - - Elastic body, 46 - - - Capacitance detector, 47 - - - Coordinate measurement stand, 48 - - - Elastic contact movement distance, 49 - - - Sample separation distance, 50 - - - Discharged sample, 51 - - - Height of liquid, 52 - - - Arm driving distance, 53 - - - Solution

The invention claimed is:

1. An automatic analyzer comprising:
a sample dispensing mechanism which moves up and down and rotates, the sample dispensing mechanism including a sample nozzle to dispense a sample into a reaction container and a supporting arm with an elastic member that elastically supports the sample nozzle;
a controller configured to control up and down movements and a rotation movement of the supporting arm to move the sample nozzle;
a photometer to measure a solution in the reaction container;
a capacitance detector set on the dispensing mechanism, the capacitance detector detecting a change of a capacitance of the sample nozzle;
a detection plate formed on the sample nozzle; and
a stop position detector set on the supporting arm, the stop position detector detecting the detection plate,
wherein the controller is further configured to calculate a contact movement distance based on a first position of the supporting arm upon determination that the capacitance detector detects that a capacitance of the sample nozzle changes more than or equal to a constant value and a second position of the supporting arm upon determination that the stop position detector detects the detection plate,
wherein the controller is further configured to move the sample nozzle downwardly toward the reaction container, stop a downward movement of the sample nozzle upon determination that the stop position detector detects the detection plate, move the supporting arm upwardly for the contact movement distance, and thereafter dispense the sample from the sample nozzle into the reaction container, and
wherein the controller is further configured to control the photometer to measure a solution including the sample in the reaction container.

2. The automatic analyzer according to claim 1, further comprising:
a coordinate measurement stand comprising a substrate and an electrically conductive surface; and
a memory, wherein
the controller is further configured to move the sample nozzle downwardly toward the coordinate measurement stand, calculate a difference between the first position of the supporting arm when the capacitance detector detects that the capacitance of the sample nozzle changes more than or equal to the constant value from contacting the coordinate measurement stand and the second position of the supporting arm when the stop position detector detects the detection plate, and store the difference as the contact movement distance in the memory.

3. The automatic analyzer according to claim 1, wherein
the controller is further configured to control a first moving speed of the sample nozzle after the sample nozzle dispenses the sample into the reaction container where the first moving speed of the sample nozzle is controlled over a liquid surface separation distance which is a distance from the contact position of the tip of the sample nozzle and the bottom of the reaction container to a separation position of the sample nozzle and a liquid surface of the sample,
the controller is further configured to control a second moving speed of the sample nozzle after the sample nozzle separates from the liquid surface, and
wherein the first moving speed of the sample nozzle is lower than the second moving speed of the sample nozzle.

4. The automatic analyzer according to claim 3, wherein the controller is further configured to determine the liquid surface separation distance when the capacitance detector detects that the sample nozzle separates from the liquid surface at the separation position.

5. The automatic analyzer according to claim 3, wherein the controller is further configured to calculate the liquid surface separation distance based on a dispensed amount of the sample from the sample nozzle into the reaction container.

6. The automatic analyzer according to claim 1, wherein the controller is further configured to move the sample nozzle downwardly toward the reaction container in which liquid is received, calculate a difference between the first position of the supporting arm when the capacitance detector detects that the capacitance of the sample nozzle changes more than or equal to the constant value and the second position of the supporting arm when the stop position detector detects the detection plate, calculate a height of a liquid in the reaction container, and calculate a value obtained by subtracting the height of the liquid from the difference as the contact movement distance.

7. The automatic analyzer according to claim 1, wherein the controller is further configured to calculate the contact movement distance based on the first position of the supporting arm causing the sample nozzle to contact a liquid surface of a liquid in the reaction container when the capacitance detector detects that the capacitance of the sample nozzle changes more than or equal to the constant value, the second position of the supporting arm when the stop position detector detects the detection plate, and a height of the liquid in the reaction container.

* * * * *